United States Patent
Slazas et al.

(10) Patent No.: US 9,149,278 B2
(45) Date of Patent: Oct. 6, 2015

(54) OCCLUSIVE DEVICE DELIVERY SYSTEM WITH MECHANICAL DETACHMENT

(71) Applicants: Robert R. Slazas, Pinecrest, FL (US); Juan A. Lorenzo, Davie, FL (US)

(72) Inventors: Robert R. Slazas, Pinecrest, FL (US); Juan A. Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 13/802,101

(22) Filed: Mar. 13, 2013

(65) Prior Publication Data
US 2014/0277078 A1    Sep. 18, 2014

(51) Int. Cl.
*A61B 17/12* (2006.01)
*A61B 17/00* (2006.01)
*A61B 19/00* (2006.01)

(52) U.S. Cl.
CPC ....... *A61B 17/1214* (2013.01); *A61B 17/12113* (2013.01); *A61B 17/12154* (2013.01); *A61B 2017/00309* (2013.01); *A61B 2017/12054* (2013.01); *A61B 2019/307* (2013.01)

(58) Field of Classification Search
CPC ............... A61B 17/12022; A61B 17/12027; A61B 17/12031; A61B 17/12099; A61B 17/12109; A61B 17/12113; A61B 17/1214; A61B 17/12145; A61B 17/12154; A61B 2017/1205; A61B 2017/12054
See application file for complete search history.

(56) References Cited

U.S. PATENT DOCUMENTS

| | | | |
|---|---|---|---|
| 5,234,437 A | 8/1993 | Sepetka |
| 5,250,071 A | 10/1993 | Palermo |
| 5,261,916 A | 11/1993 | Engelson |
| 5,263,964 A | 11/1993 | Purdy |
| 5,312,415 A | 5/1994 | Palermo |
| 5,344,426 A | 9/1994 | Lau et al. |
| 5,380,304 A | 1/1995 | Parker |
| 5,562,698 A | 10/1996 | Parker |
| 5,601,600 A | 2/1997 | Ton |
| 5,700,253 A | 12/1997 | Parker |
| 5,746,769 A | 5/1998 | Ton et al. |
| 5,762,615 A | 6/1998 | Weier |
| 5,788,707 A | 8/1998 | Del Toro et al. |

(Continued)

FOREIGN PATENT DOCUMENTS

| | | |
|---|---|---|
| EP | 1 813 196 | 8/2007 |
| EP | 2 630 936 | 8/2013 |

OTHER PUBLICATIONS

European Search Report for counterpart EP Application Serial No. 14159234 (Jul. 17, 2014)(7 pages).

(Continued)

*Primary Examiner* — Ryan Severson
(74) *Attorney, Agent, or Firm* — Cohen & Hildebrand, PLLC

(57) ABSTRACT

A delivery system for an embolic coil including a delivery tube having a lumen. A proximal coil junction is disposed between the delivery tube and the embolic coil. Insertable through the lumen and extending proximally beyond the proximal end of the delivery tube is a detachable wire with a terminating feature disposed on its distal end. At least one stretch resistant member is disposed within a lumen formed by the embolic coil. A distal end of each of the at least one stretch resistant members is secured to a distal end of the embolic coil, while each of the at least one stretch resistant members is also secured proximate the proximal end of the embolic coil. The distal end of the delivery tube is retained by the wire physically against without being attached in any way to the proximal junction.

2 Claims, 5 Drawing Sheets

(56) References Cited

U.S. PATENT DOCUMENTS

| | | |
|---|---|---|
| 5,800,455 A | 9/1998 | Palermo et al. |
| 5,853,418 A | 12/1998 | Ken et al. |
| 5,925,059 A | 7/1999 | Palermo et al. |
| 6,063,100 A | 5/2000 | Diaz et al. |
| 6,099,546 A | 8/2000 | Gia |
| 6,113,607 A | 9/2000 | Lau et al. |
| 6,179,857 B1 | 1/2001 | Diaz et al. |
| RE37,117 E | 3/2001 | Palermo |
| 6,612,012 B2 | 9/2003 | Mitelberg et al. |
| 6,673,106 B2 | 1/2004 | Mitelberg et al. |
| 6,818,013 B2 | 11/2004 | Mitelberg et al. |
| 6,833,003 B2 | 12/2004 | Jones et al. |
| 6,866,679 B2 | 3/2005 | Kusleika |
| 6,907,298 B2 | 6/2005 | Smits et al. |
| 6,955,685 B2 | 10/2005 | Escamilla et al. |
| 6,960,227 B2 | 11/2005 | Jones et al. |
| 6,960,228 B2 | 11/2005 | Mitelberg et al. |
| 6,966,892 B2 | 11/2005 | Gandhi et al. |
| 7,001,422 B2 | 2/2006 | Escamilla et al. |
| 7,037,331 B2 | 5/2006 | Mitelberg et al. |
| 7,201,769 B2 | 4/2007 | Jones et al. |
| 7,309,351 B2 | 12/2007 | Escamilla et al. |
| 7,367,987 B2 * | 5/2008 | Balgobin et al. ............ 606/200 |
| 7,371,251 B2 * | 5/2008 | Mitelberg et al. ............ 606/200 |
| 7,371,252 B2 * | 5/2008 | Balgobin et al. ............ 606/200 |
| 7,377,932 B2 * | 5/2008 | Mitelberg et al. ............ 606/200 |
| 7,422,569 B2 * | 9/2008 | Wilson et al. ............ 604/113 |
| 7,572,246 B2 * | 8/2009 | Wilson et al. ............ 604/113 |
| 7,608,058 B2 * | 10/2009 | Wilson et al. ............ 604/113 |
| 7,608,089 B2 * | 10/2009 | Wallace et al. ............ 606/200 |
| 7,780,695 B2 * | 8/2010 | Jones et al. ............ 606/200 |
| 7,794,487 B2 | 9/2010 | Majercak et al. |
| 7,799,052 B2 * | 9/2010 | Balgobin et al. ............ 606/200 |
| 7,811,305 B2 * | 10/2010 | Balgobin et al. ............ 606/200 |
| 7,819,891 B2 * | 10/2010 | Balgobin et al. ............ 606/200 |
| 7,819,892 B2 * | 10/2010 | Balgobin et al. ............ 606/200 |
| 7,901,444 B2 | 3/2011 | Slazas |
| 7,918,872 B2 * | 4/2011 | Mitelberg et al. ............ 606/200 |
| 7,942,898 B2 | 5/2011 | Ewers et al. |
| 7,985,238 B2 * | 7/2011 | Balgobin et al. ............ 606/200 |
| 8,002,789 B2 * | 8/2011 | Ramzipoor et al. ............ 606/200 |
| 8,016,872 B2 | 9/2011 | Parker |
| 8,147,534 B2 | 4/2012 | Berez et al. |
| 8,206,413 B2 * | 6/2012 | Jones et al. ............ 606/200 |
| 8,333,796 B2 | 12/2012 | Tompkins et al. |
| 8,574,260 B2 * | 11/2013 | Mitelberg et al. ............ 606/200 |
| 8,926,650 B2 * | 1/2015 | Que et al. ............ 606/200 |
| 2004/0034363 A1 * | 2/2004 | Wilson et al. ............ 606/108 |
| 2004/0199175 A1 | 10/2004 | Jaeger et al. |
| 2005/0043755 A1 * | 2/2005 | Wilson et al. ............ 606/200 |
| 2006/0025802 A1 * | 2/2006 | Sowers ............ 606/200 |
| 2006/0025803 A1 * | 2/2006 | Mitelberg et al. ............ 606/200 |
| 2006/0135986 A1 | 6/2006 | Wallace et al. |
| 2006/0241684 A1 * | 10/2006 | Wilson et al. ............ 606/200 |
| 2006/0241685 A1 * | 10/2006 | Wilson et al. ............ 606/200 |
| 2006/0271086 A1 * | 11/2006 | Ramzipoor et al. ............ 606/191 |
| 2006/0276823 A1 * | 12/2006 | Mitelberg et al. ............ 606/200 |
| 2006/0276824 A1 * | 12/2006 | Mitelberg et al. ............ 606/200 |
| 2006/0276825 A1 * | 12/2006 | Mitelberg et al. ............ 606/200 |
| 2006/0276826 A1 * | 12/2006 | Mitelberg et al. ............ 606/200 |
| 2006/0276827 A1 * | 12/2006 | Mitelberg et al. ............ 606/200 |
| 2006/0276828 A1 * | 12/2006 | Balgobin et al. ............ 606/200 |
| 2006/0276829 A1 * | 12/2006 | Balgobin et al. ............ 606/200 |
| 2006/0276830 A1 * | 12/2006 | Balgobin et al. ............ 606/200 |
| 2006/0276832 A1 * | 12/2006 | Balgobin et al. ............ 606/200 |
| 2006/0276833 A1 * | 12/2006 | Balgobin et al. ............ 606/200 |
| 2006/0276834 A1 * | 12/2006 | Balgobin et al. ............ 606/200 |
| 2007/0005099 A1 * | 1/2007 | Jones et al. ............ 606/200 |
| 2007/0010849 A1 * | 1/2007 | Balgobin et al. ............ 606/200 |
| 2007/0010850 A1 * | 1/2007 | Balgobin et al. ............ 606/200 |
| 2007/0118172 A1 * | 5/2007 | Balgobin et al. ............ 606/200 |
| 2008/0119887 A1 | 5/2008 | Que et al. |
| 2008/0132939 A1 * | 6/2008 | Wilson et al. ............ 606/200 |
| 2008/0133028 A1 * | 6/2008 | Wilson et al. ............ 623/23.76 |
| 2008/0140111 A1 * | 6/2008 | Wilson et al. ............ 606/200 |
| 2008/0140178 A1 | 6/2008 | Rasmussen et al. |
| 2008/0140219 A1 * | 6/2008 | Wilson et al. ............ 623/23.76 |
| 2008/0140220 A1 * | 6/2008 | Wilson et al. ............ 623/23.76 |
| 2008/0147201 A1 * | 6/2008 | Wilson et al. ............ 623/23.76 |
| 2008/0228215 A1 | 9/2008 | Strauss et al. |
| 2008/0300616 A1 * | 12/2008 | Que et al. ............ 606/191 |
| 2008/0306503 A1 | 12/2008 | Que et al. |
| 2008/0306504 A1 | 12/2008 | Win et al. |
| 2009/0177261 A1 * | 7/2009 | Teoh et al. ............ 623/1.11 |
| 2009/0292303 A1 * | 11/2009 | Wilson et al. ............ 606/158 |
| 2010/0004675 A1 * | 1/2010 | Wilson et al. ............ 606/200 |
| 2010/0042133 A1 * | 2/2010 | Ramzipoor et al. ............ 606/191 |
| 2010/0160944 A1 | 6/2010 | Teoh et al. |
| 2010/0286723 A1 * | 11/2010 | Jones et al. ............ 606/200 |
| 2011/0060360 A1 * | 3/2011 | Mitelberg et al. ............ 606/200 |
| 2011/0178589 A1 | 7/2011 | Andreas et al. |
| 2011/0270374 A1 | 11/2011 | Orr et al. |
| 2011/0301702 A1 | 12/2011 | Rust et al. |
| 2011/0313443 A1 | 12/2011 | Lorenzo et al. |
| 2012/0209310 A1 | 8/2012 | Chen et al. |
| 2013/0138136 A1 * | 5/2013 | Beckham et al. ............ 606/200 |
| 2013/0261659 A1 * | 10/2013 | Lorenzo ............ 606/200 |
| 2014/0277078 A1 * | 9/2014 | Slazas et al. ............ 606/200 |

OTHER PUBLICATIONS

Copending, co-owned U.S. Appl. No. 13/799,437, filed Mar. 13, 2013.

* cited by examiner

OCCLUSIVE DEVICE DELIVERY SYSTEM WITH MECHANICAL DETACHMENT

BACKGROUND OF THE INVENTION

1. Field of the Invention

The present invention relates to occlusive devices (e.g., embolic coils) for implantation within a blood vessel of a body. In particular, the present invention relates to an improved mechanical detachment for an embolic coil delivery system in the treatment of blood vessel disorders.

2. Description of Related Art

Vascular disorders and defects such as aneurysms and other arterio-venous malformations are especially difficult to treat when located near critical tissues or where ready access to malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

Alternative treatments include vasculature occlusion devices, such as embolic coils, deployed using catheter delivery systems. In such systems used to treat cranial aneurysms, the distal end of an embolic coil delivery catheter is inserted into non-cranial vasculature of a patient, typically through a femoral artery in the groin, and guided to a predetermined delivery site within the cranium.

Multiple embolic coils of various lengths, generally approximately 1 cm to approximately 30 cm, and preselected stiffness often are packed sequentially within a cranial aneurysm to limit blood flow therein and to encourage embolism formation. Typically, physicians first utilize stiffer coils to establish a framework within the aneurysm and then select more flexible coils to fill spaces within the framework. Ideally, each coil conforms both to the aneurysm and to previously implanted coils. Each successive coil is selected individually based on factors including stiffness, length, and preformed shape which the coil will tend to assume after delivery.

During implantation, the physician manipulates each embolic coil until it is in a satisfactory position, as seen by an imaging technique such as fluoroscopic visualization, before detaching the coil from the delivery system. It is beneficial for both ends of each coil to remain positioned within the aneurysm after delivery; otherwise, a length of coil protruding into the main lumen of the blood vessel invites undesired clotting external to the aneurysm. After each successive coil is detached, the next coil is subject to an increasing risk of becoming entangled in the growing mass of coils, thereby restricting the depth of insertion for that coil into the aneurysm.

Difficulties may arise due to stretching of the embolic coils during repositioning or attempted retrieval of the coils, especially if the coil becomes entangled and complete insertion of the coil into the aneurysm is not accomplished. If pulling forces applied to a coil exceed its elastic limit, the coil will not return to its original shape. A stretched coil exhibits diminished pushability or retractability, and becomes more difficult to manipulate into an optimal position or to be removed. Moreover, a stretched coil occupies less volume than an unstretched coil, which increases the number of coils needed to sufficiently pack the aneurysm to encourage formation of a robust embolus positioned wholly within the aneurysm. To avoid such problems stretch resistance devices are used, such as that disclosed in U.S. Pat. No. 5,853,418, herein incorporated by reference in its entirety, having a primary coil and an elongated stretch-resisting member fixedly attached to the primary coil in at least two locations.

In order to deliver the vaso-occlusive coils to a desired site, e.g., an aneurysm, in the vasculature, it is well-known to first position a small profile, delivery catheter or micro-catheter at the targeted site using fluoroscopy, ultrasound, or other method of steerable navigation. A delivery or "pusher" wire is then passed through a proximal end of the catheter lumen, until a vaso-occlusive coil coupled to a distal end of the pusher wire is extended out of the distal end opening of the catheter and into the blood vessel at the targeted site. The vaso-occlusive device is then released or detached from the end pusher wire, and the pusher wire is withdrawn in a proximal direction back through the catheter. Depending on the particular needs of the patient, another occlusive device may then be pushed through the catheter and released at the same site in a similar manner.

Several conventional methods are used to detach the wire from the embolic coil once it has been properly positioned at the targeted site in the blood vessel. One known way to release a vaso-occlusive coil from the end of the pusher wire is through the use of an electrolytically severable junction, which is an exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone disintegrates due to electrolysis.

One disadvantage of occlusive devices that are deployed using electrolytic detachment is that the electrolytic process requires a certain amount of time to elapse to effectuate release of the occlusive element. This time lag is also disadvantageous for occlusive delivery devices that utilize thermal detachment such as that described in U.S. Pat. No. 6,966,892, which is herein incorporated by reference in its entirety.

Another conventional detachment technique during delivery of a vaso-occlusive device involves the use of fluid pressure (e.g., hydraulic detachment) to release an embolic coil once it is properly positioned, as described in U.S. Pat. Nos. 6,063,100 and 6,179,857, each of which is herein incorporated by reference in their entirety.

The main problems associated with current detachment schemes are reliability of detachment, speed of detachment, convenience of detaching mechanism (e.g., hydraulic detachment requires a high pressure syringe, while electrolytic detachment requires a battery operated box), and length/stiffness of the distal section.

It is therefore desirable to develop an improved mechanical detachment for an embolic coil delivery system that solves the aforementioned problems associated with conventional devices.

SUMMARY OF THE INVENTION

An aspect of the present invention relates to an improved mechanical detachment system for delivery of an embolic coil that is simpler, more reliable, quicker, more convenient and having shorter stiff sections than that in conventional mechanical detachment systems.

Another aspect of the present invention is directed to a delivery system for an embolic coil including a delivery tube having a lumen defined axially therethrough. A proximal coil junction is disposed between the delivery tube and the embolic coil. Insertable through the lumen and extending proximally beyond the proximal end of the delivery tube is a detachable wire having a terminating feature disposed on its distal end. At least one stretch resistant member is disposed within a lumen formed by the embolic coil. A distal end of each of the at least one stretch resistant members being secured to a distal end of the embolic coil, while each of the at least one stretch resistant members is also secured proximate the proximal end of the embolic coil. The distal end of the delivery tube is retained by the wire physically against without being attached in any way to the proximal junction.

Yet another aspect of the present invention relates to a delivery system for an embolic coil including a delivery tube having a lumen defined axially therethrough. A proximal coil junction is disposed between the delivery tube and the embolic coil. The proximal coil junction is a joint made out of at least one of an adhesive, an epoxy and/or a polymer; and wherein a strength of the adhesive or epoxy, as well as a durometer of the polymer used for the joint is less than a buckling strength of the delivery tube. Insertable through the lumen and extending proximally beyond the proximal end of the delivery tube is a detachable wire having a terminating feature disposed on its distal end. At least one stretch resistant member is disposed within a lumen formed by the embolic coil. A distal end of each of the at least one stretch resistant members being secured to a distal end of the embolic coil, while each of the at least one stretch resistant members is also secured proximate the proximal end of the embolic coil. The distal end of the delivery tube is retained by the wire physically against without being attached in any way to the proximal junction.

Still another aspect of the present invention is directed to a method of using the delivery system in accordance with the preceding paragraph including the steps of pulling the proximal end of the wire with a sufficient predetermined force until either: (i) the terminating feature pulls out from the joint; or (ii) the wire severs at a targeted mechanically weakened section. Then the embolic coil is releasable from the wire.

While still another aspect of the present invention is directed to a delivery system for an embolic coil including a delivery tube having a lumen defined axially therethrough. A proximal coil junction is disposed between the delivery tube and the embolic coil. Insertable through the lumen and extending proximally beyond the proximal end of the delivery tube is a detachable wire having a terminating feature disposed on its distal end. At least one stretch resistant member is disposed within a lumen formed by the embolic coil. A distal end of each of the at least one stretch resistant members being secured to a distal end of the embolic coil, while each of the at least one stretch resistant members is also secured proximate the proximal end of the embolic coil. The distal end of the delivery tube is retained by the wire physically against without being attached in any way to the proximal junction. A coil connecting member is threaded through the terminating feature and secured to the proximal coil junction.

And yet another aspect of the present invention is directed to a method of using the delivery system in accordance with the preceding paragraph including the steps of pulling the proximal end of the wire with a sufficient predetermined force until the coil connecting member severs where it is threaded through the terminating feature. Then the embolic coil is releasable from the wire.

And in still another aspect of the present invention. The delivery system for an embolic coil includes a delivery tube having a lumen defined axially therethrough. A proximal coil junction is disposed between the delivery tube and the embolic coil. Insertable through the lumen and extending proximally beyond the proximal end of the delivery tube is a detachable wire having a terminating feature disposed on its distal end. The proximal coil junction comprises a two piece mating adapter including a first component secured to the distal end of the delivery tube and a second component secured to the proximal end of the embolic coil. The two-piece mating adapter has a first channel defined longitudinally therethrough for receiving therein the terminating feature of the wire and a second channel defined traverse to and intersecting with the first channel. The delivery system further includes a coil connecting member receivable in the second channel and threadable through the terminating feature of the wire. At least one stretch resistant member is disposed within a lumen formed by the embolic coil. A distal end of each of the at least one stretch resistant members being secured to a distal end of the embolic coil, while each of the at least one stretch resistant members is also secured proximate the proximal end of the embolic coil. The distal end of the delivery tube is retained by the wire physically against without being attached in any way to the proximal junction.

While yet another aspect of the present invention is directed to a method for using the delivery system in the preceding paragraph including the steps of removing the coil connecting member completely from the second channel of the two piece mating adapter and the terminating feature of the wire. Thereafter the wire is pulled in a proximal direction to separate the second component attached to the embolic coil from that of the first component attached to the delivery tube.

In yet another aspect of the present invention is directed to a delivery system for an embolic coil including a delivery tube having a lumen defined axially therethrough. A proximal coil junction is disposed between the delivery tube and the embolic coil. Insertable through the lumen and extending proximally beyond the proximal end of the delivery tube is a detachable wire having a terminating feature disposed on its distal end. At least one stretch resistant member is disposed within a lumen formed by the embolic coil. A distal end of each of the at least one stretch resistant members being secured to a distal end of the embolic coil, while each of the at least one stretch resistant members is also secured proximate the proximal end of the embolic coil. The distal end of the delivery tube is retained by the wire physically against without being attached in any way to the proximal junction. An aperture is defined longitudinally through the proximal coil junction. The terminating feature of the wire has a maximum diameter greater than a diameter of the aperture defined in the proximal coil junction forming a friction fit therebetween retaining the terminating feature of the wire therein.

While still yet another aspect of the present invention relates to a method for using the delivery system in the preceding paragraph by pulling the proximal end of the wire with a sufficient predetermined force to overcome the friction fit between the maximum diameter of the terminating feature of the wire and the aperture of the proximal coil junction. Thereafter, the wire along with its terminating feature is released from the embolic coil.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

The terms "proximal"/"proximally" and "distal"/"distally" refer to a direction closer to or away from, respectively, an operator (e.g., surgeon, physician, nurse, technician, etc.) who would insert the medical device into the patient, with the tip-end (i.e., distal end or leading end) of the device inserted inside a patient's body. Thus, for example, a "proximal direction" would refer to the direction towards the operator, whereas "distal direction" would refer to the direction away from the operator towards the leading or tip-end of the medical device.

Figure 1A:
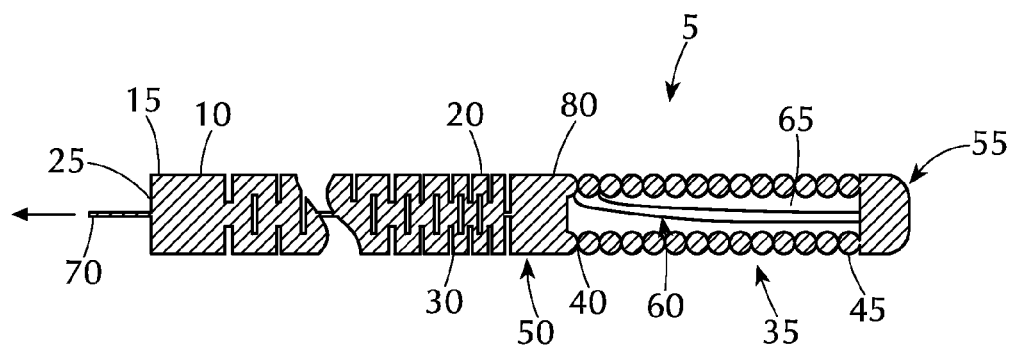
FIG. 1A is a cross-sectional view of a first embodiment of the present inventive an embolic coil delivery system in which the embolic coil is secured to the distal terminating feature of the wire via a proximal coil junction (e.g., relatively low strength and/or relatively low durometer adhesive, epoxy or polymer joint) disposed therebetween and the proximal end of each of the stretch resistant members is looped in the proximal coil loop/winding of the embolic coil.

FIG. 1A is a cross-sectional view of a first exemplary mechanical detachment system for delivery of an embolic coil in accordance with the present invention. The detachment system 5 includes a flexible delivery tube 10 (e.g., hypotube, or catheter) having a proximal end 15, an opposite distal end 20 and a lumen 25 defined axially therethrough. Tube 10 may be either a single integral construction or otherwise multiple components or sections such as a proximal section made of a first material (e.g., stainless steel) and a flexible distal section made of a second material (e.g., Nitinol), different from that of the first material, and connected to the proximal section of the tube.

A plurality of slits 30 substantially perpendicular to the longitudinal direction are defined in the tube 10 in a discontinuous, interrupted configuration to retain the integrity of the distal flexible section while enhancing flexibility and minimizing compression/buckling of the delivery tube when the wire is pulled proximally therefrom. Factors such as the arrangement, number and spacing between slits 30 determines the level or degree of stiffness/flexibility of the tube 10. In the case of the tube 10 configured as multiple components or sections, the interrupted slits 30 are defined only in the distal section of the tube 10. These interrupted slits 30 minimize the axial compression of the tube during actuation of the detachment system 5.

Figure 1B:
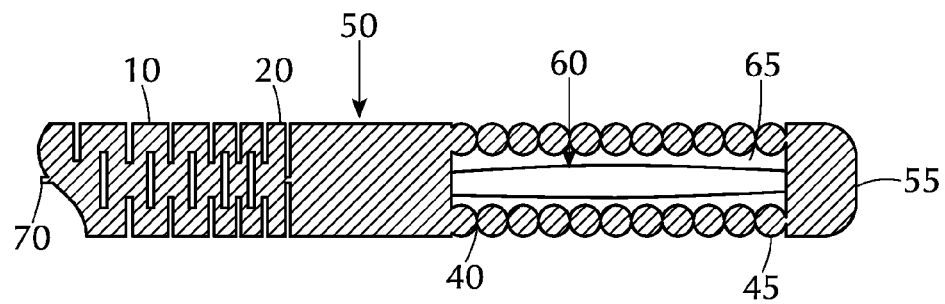
FIG. 1B is a cross-sectional view of an alternative embodiment of the embolic coil delivery system in FIG. 1A, wherein a proximal end of each of the stretch resistant members is embedded in the proximal coil junction.

An open proximal end of an occlusive device, typically a helical embolic coil 35 formed by a series of loops/windings defining a coil lumen 65, is attached to the distal end 20 of the tube 10 by a proximal coil junction 50 (e.g., a relatively low strength and/or relatively low durometer adhesive, epoxy or polymer joint. That is, the relatively low strength of the epoxy/adhesive, or the relatively low durometer of the polymer used to fill that junction (which is related to its tear-out strength) is preferably less than the buckling strength of the delivery tube. Opposite its open proximal end 40, a distal end 45 of the embolic coil 35 is closed off by a distal bead 55. One or more stretch resistant (SR) members 60, e.g., suture filaments, disposed in the coil lumen 65 provide stretch resistance when excessive pulling forces are applied to the embolic coil 35 during implantation in a patient. Preferably, each stretch resistant member 60 extends longitudinally the entire length of the coil lumen 65 from its proximal end 40 to its distal end 45 to minimize excessive elongation. In an embodiment of the present invention depicted in FIG. 1A, each stretch resistant suture filament 60 is threaded through the coil lumen 65 with its proximal end looped around an open proximal coil loop/winding of the embolic coil 35 and its opposite distal end is secured to the distal end 45 (e.g., distal bead 55) of the embolic coil 35. An alternative embodiment is shown in FIG. 1B, which differs from that in FIG. 1A, in that the proximal end of each stretch resistant suture filament 60 is embedded into the proximal coil junction 50 disposed between the tube 10 and embolic coil 35, rather than looped in an open proximal winding of the embolic coil 35.

Figure 1C:
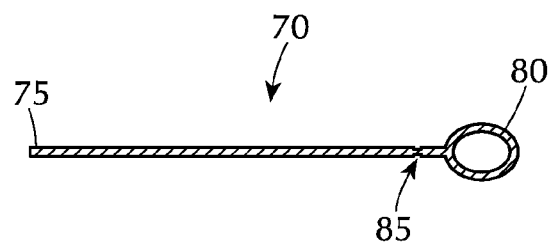
FIG. 1C an enlarged perspective view of an exemplary wire in FIG. 1A.

Referring to FIG. 1C, is an enlarged view of an exemplary wire 70 having a free proximal end 75 and an opposite end with a distal terminating feature 80 (e.g., a closed shape (loop, lasso or ring) or an open shape (hook)). Wire 70 is freely movable through the lumen 25 of the delivery tube 10 with the distal terminating feature 80 secured within the proximal end of the proximal coil junction 50 (e.g., epoxy or adhesive joint) joining the delivery tube 10 to the embolic coil 35. Wire 70 has a length that exceeds that of the tube 10 in a longitudinal direction so that its proximal end 75 extends proximally beyond the proximal end 15 of the tube 10. Once the embolic coil 35 has been properly positioned at a desired location in a blood vessel, the embolic coil 35 is detachable from the delivery tube 10 by proximally pulling its free proximal end 75 until the terminating feature 80 disposed at its opposite end becomes detached/separates/pulls out from the proximal coil junction 50 (e.g., adhesive joint) thereby releasing the embolic coil 35 at the targeted site within the blood vessel. Instead of dislodging the terminating feature 80 from the adhesive proximal coil junction 50, wire 70 may be designed to have a mechanically weakened section 85 (typically a section of wire having a reduced cross-section relative to the remaining part of the wire). Upon application of a predetermined force on the proximal end 75 of the wire 70 in the proximal direction, the wire 70 will separate at the location of the weakened section 85 thereby releasing the embolic coil (together with the proximal coil junction and distal terminating feature of the wire secured to the embolic coil). The degree of force required to separate the wire at the weakened section 85 depends on one more of factors including material selection and/or cross-sectional reduction in diameter.

Figure 2A:
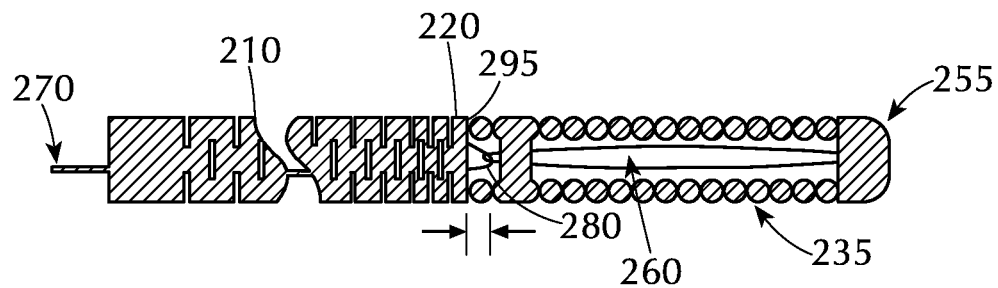
FIGS. 2A-2C are a series of sequential cross-sectional views of a second embodiment of the present inventive embolic coil delivery system in which the embolic coil is secured to the distal terminating feature of the wire by stretch resistant members whose proximal end is threaded therethrough.
Figure 2B:
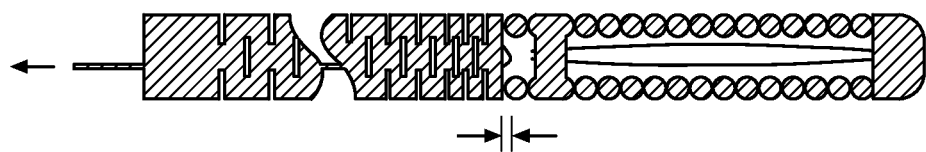
Figure 2C:

An alternative embodiment is depicted in the sequential illustrations depicted in FIG. 2A-2C in which the embolic coil is secured to the distal terminating feature of the wire via the proximal ends of SR members being threaded therethrough. Specifically, the wire 270 is introduced into the proximal end of the lumen 225 until its distal terminating feature 280 (closed shape (loop, lasso or ring) or open shape (hook)) is disposed between the distal end 220 of the delivery tube 210 and the proximal coil junction 250. Once the wire 270 is properly positioned, the distal terminating feature 280 is secured, e.g., via an adhesive or epoxy, to the distal end 220 of the delivery tube 210 at an attachment point 295, as shown in FIG. 2A. In contrast to the proximal coil junction 50 in FIG. 1A, the proximal coil junction 250 in FIG. 2A is a mechanical structure having an opening defined axially therethrough. A distal end of each SR member 260 is secured to the distal bead 255 at the distal end of the embolic coil 235. An intermediate section of each SR member 260 is secured (e.g., via an adhesive or epoxy) to the embolic coil 235 proximate its proximal end (i.e., proximate the proximal junction 250). An opposite proximal end of each SR member 260 passes through the opening defined axially through the proximal coil junction 250 and is threaded through the distal terminating feature 280.

In this embodiment depicted in FIGS. 2A-2D, proximal coil junction 250 has a multi-functional purpose of: (i) securing the SR members 260 to the embolic coil 235; (ii) minimizing any slack on the SR members 260 between the proximal coil junction 250 and the distal terminating feature 280; and (iii) retaining the stretch resistance characteristics of the embolic coil 235 post detachment from the wire 270.

Detachment of the embolic coil 235 from the wire 270 is realized by pulling the proximal end of the wire 270 in a proximal direction, as identified by the arrow in FIG. 2B, until a mechanical severing occurs at one of: (i) the weakest point along the wire 270, (ii) the attachment point 295, or (iii) along the SR member 260 thereby releasing the embolic coil 235, as shown in FIG. 2C. As previously noted, mechanical failure may be targeted to a predetermined weakened point (e.g., reduced diameter) disposed at a desired location along the wire 270, SR member 260 or at the attachment point 295.

Figure 2D:
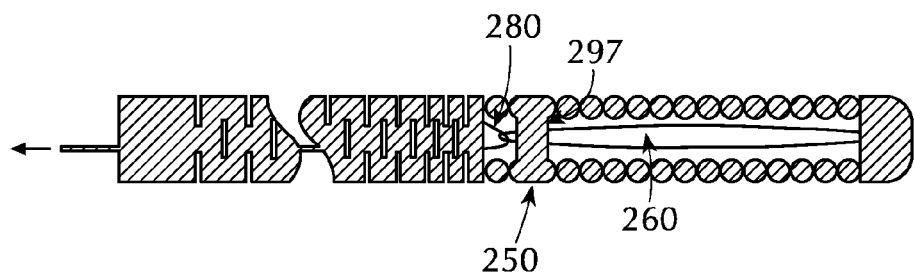
FIG. 2D is a cross-sectional view of an alternative embodiment of the embolic coil delivery system in FIGS. 2A-2C in which the embolic coil is secured to the distal terminating feature of the wire via a separate coil connecting member attached to the proximal end of the proximal coil junction and threaded therethrough.

In FIG. 2A, embolic coil 235 is attached to the wire 270 via SR member 260 being threaded through the terminating feature 280 (e.g., closed loop). Independent of the SR member 260, the proximal end of the embolic coil 235 may, alternatively, be attached to the distal end of the wire 270 via a separate coil connecting member 297 (preferably U-shaped) that is threaded through the distal terminating feature 280 and secured within the proximal coil junction 250, as shown in FIG. 2D. Coil connecting member 297 may be made of a polymer or any other material that breaks at forces less than those required to break the distal terminating feature 280 or to buckle the slotted delivery tube 210. Also secured within the proximal coil junction 250 is the proximal end of each of the SR members 260. Of course, the SR members 260 could otherwise be secured in place by threading its proximal ends through an open primary winding of the embolic coil 235 (as depicted in FIG. 1A).

Figure 2E:
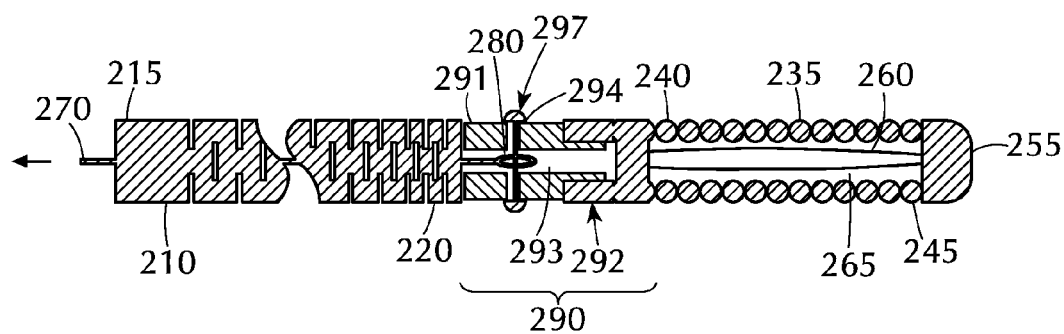
FIG. 2E is a cross-sectional view of an alternative embodiment of the embolic coil delivery system in FIGS. 2A-2C in which the embolic coil is secured to the distal terminating feature of the wire via a two piece mating adapter and a releasable coil connecting member disposed transversely through the adapter and threaded through the distal terminating feature.

In still a further variation of the embodiment shown in FIG. 2E, a two piece mating adapter 290 may be used to connect the distal end of the delivery tube 210 and the proximal end of the embolic coil 235. In the exemplary embodiment illustrated in FIG. 2E, mating adapter 290 includes a first component 291 mounted to the distal end of the delivery tube 210 and a second component 292 mounted to the proximal end of the embolic coil 235. The adapter 290 has a first channel 293 defined longitudinally therein. A second channel 294 is defined transverse therethrough the adapter 290 and intercepts that of the first channel 293. Detachment wire 270 is introduced into the first channel 291 of the adapter 290 until its distal terminating feature 280 (e.g., a lasso, loop, ring or any other substantially closed shape) is substantially aligned with the second channel 294. A coil connecting member 297 (e.g., a pin or rod) is then threaded through the second channel 294 and passes through the distal terminating feature 280. The coil connecting member 297 is made of a polymer or other material which breaks or separates at forces lower than the forces required to break the distal terminating feature 280. Detachment of the embolic coil 235 is achieved by pulling the proximal end of the wire 270 in a proximal direction until the coil connecting member 297 severs releasing the embolic coil 235 at its desired location within a blood vessel.

In the second embodiment depicted in FIG. 2A, the distal terminating feature 280 extends from the distal end of the delivery tube 10 but does not pass through the proximal coil junction 250. In a third embodiment of the embolic coil delivery system in accordance with the present invention as shown in FIGS. 3A-3E, distal terminating feature 380 of the wire 370 is sized and shaped to be restrained by an interference, press or friction fit within the aperture 396 defined axially through the proximal coil junction 350. One possible configuration for the distal terminating feature 380, as illustrated in the figures, is a triangle tapered longitudinally with its distal end having a maximum diameter greater than its proximal end. Specifically, the maximum diameter of the distal terminating feature 380 is greater than the aperture 396 defined in the proximal coil junction 330 restraining it via an interference, press or friction fit from passing freely therethrough, except upon the application a predetermined pulling force on the wire in a proximal direction. The force required to pull the distal terminating feature 380 from the aperture 396 of the proximal coil junction 330 depends on such factors as the materials of each and the dimension interference therebetween. Taking such factors into consideration, a pull-out force is provided that is less than the buckling strength of the delivery tube 310, but greater than typical manipulation forces exerted on the embolic coil 235 during placement.

Figure 3A:
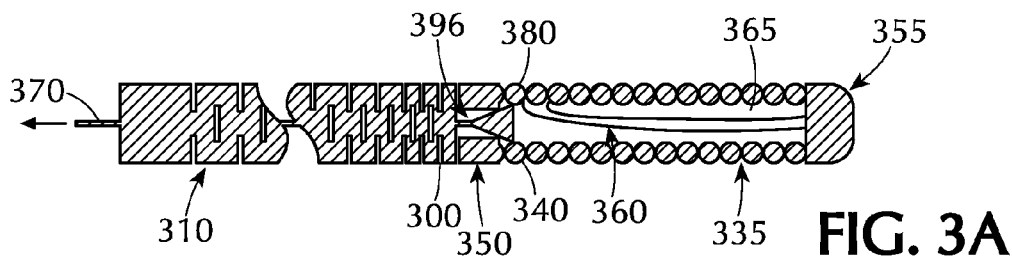
FIG. 3A is a cross-sectional view of a third embodiment of the present inventive embolic coil delivery system in which the embolic coil is secured to the distal terminating feature of the wire via an interference fit with the proximal coil junction and a proximal end of each of the stretch resistant members is looped in the proximal coil loop/winding of the embolic coil.
Figure 3B:
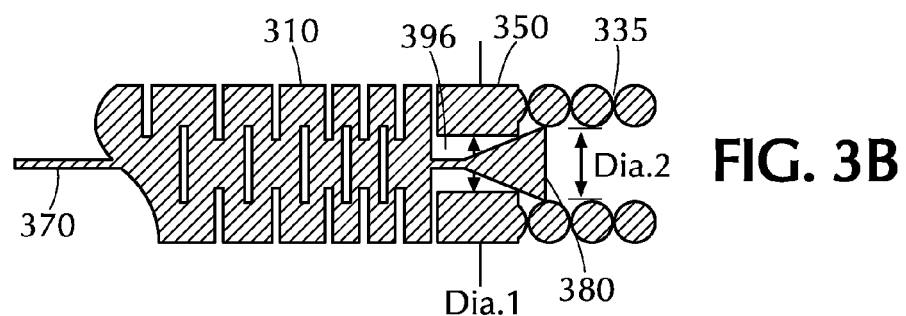
FIGS. 3B-3D are a series of enlarged sequential cross-sectional view of the embolic coil delivery system in FIG. 3A.

The proximal coil junction 350 is adhered to the proximal end of the embolic coil 335. In turn, the embolic coil 335 is secured to the distal end of the wire 370 by an interference fit between distal terminating feature 380 and the interior surface of aperture 396 defined in the proximal coil junction 350. Prior to being introduced into a blood vessel, at least that portion of distal terminating feature 380 having its maximum diameter is preferably disposed within the lumen 365 of the embolic coil 335 beyond the distal end of the proximal coil junction 350 in a distal direction, as shown in FIG. 3A. It is also contemplated and with the intended scope of the present invention for at least that portion of distal terminating feature 380 having its maximum diameter be disposed only within the aperture 396 (without extending into the coil lumen 365) of the proximal coil junction 335 as long as the provided pull-out force of the wire 370 in a proximal direction from that position exceeds typical manipulation forces during placement of the embolic coil 335. An enlarged partial view of the interference, press or friction fit between the feature 380 and the interior surface of the lumen 365 of the embolic coil 335 is depicted in FIG. 3B. To insure an interference, press or friction fit the maximum diameter of the distal terminating feature 380 is greater than an inner diameter of the aperture 396 of the proximal coil junction 350.

Figure 3C:
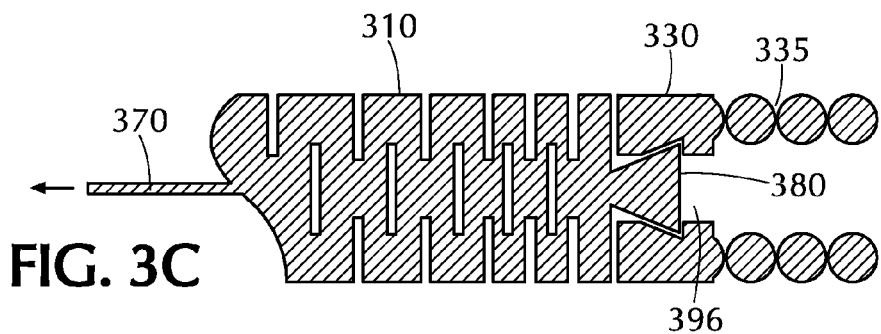
Figure 3D:
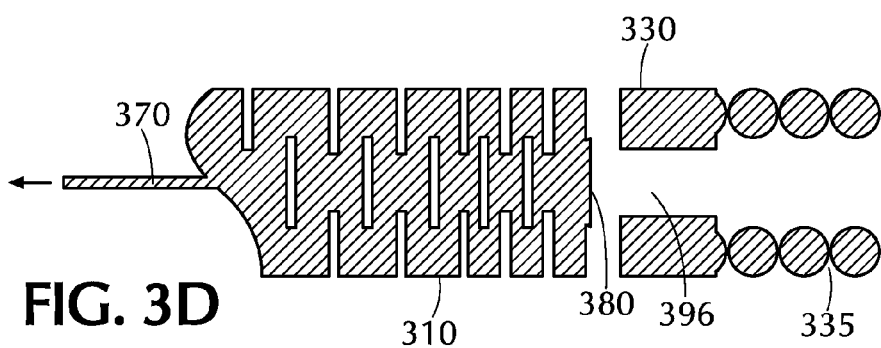
Figure 3E:
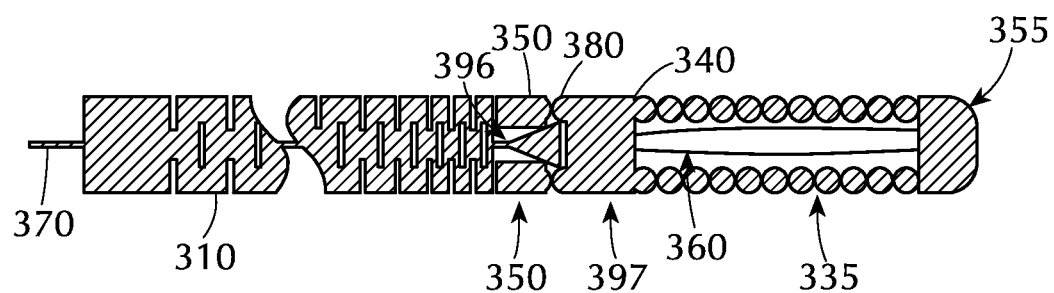
FIG. 3E is a cross-sectional view of an alternative embodiment of the embolic coil delivery system in FIGS. 3A-3D in which the proximal ends of the stretch resistant members are secured to an intermediate coil junction.

Detachment of the embolic coil 335 is achieved by pulling the proximal end of the wire 370 in a proximal direction with a predetermined sufficient force required to overcome the interference, press or friction fit of the distal terminating feature 380 with the aperture 396 of the proximal coil junction 350 allowing the distal terminating feature 380 to pass therethrough, as illustrated in FIG. 3C. Further pulling in a proximal direction on the wire 370 allows it to pass completely through the lumen 325 defined in the delivery tube 310, as shown in FIG. 3D, releasing the embolic coil 335 together with the proximal coil junction 350. In the exemplary embodiment shown in FIG. 3A, the proximal end 340 of the embolic coil 335 is attached to the distal end 320 of the delivery tube 310 via the proximal coil junction 350 (e.g., relatively low strength adhesive or epoxy joint) and the proximal ends of the SR members 360 are looped around an open proximal winding of the embolic coil 335. As an alternative configuration, in FIG. 3E the proximal end 340 of the embolic coil 335 is attached to a separate intermediate coil junction 397 which, in turn, is connected to the delivery tube 310 via the proximal coil junction 350. In this configuration the proximal ends of the SR members 360 are secured directly to the intermediate coil junction 395 (e.g., via an adhesive or epoxy).

Figure 3F:
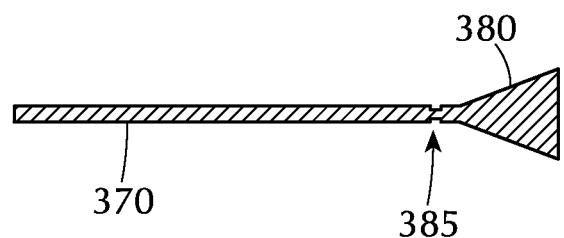
FIG. 3F is an enlarged view of the wire of FIG. 3A.

Rather than completely removing the wire 370 (including its distal terminating feature 380) from the embolic coil 335, alternatively, a mechanically weakened section may be provided at a targeted location along the wire 370 to promote separation thereof upon applying a sufficient predetermined force. FIG. 3F is an enlarged view of the wire 370 of FIG. 3A with a targeted mechanically weakened section 385 to allow separation of the wire securing the coil at the targeted location. When the embolic coil is released from the delivery device, at least the distal terminating feature 380 remains in the aperture 396 of the proximal coil junction 350. The predetermined force necessary to separate the wire 370 at its targeted mechanically weakened section 385 is based on the material selection and/or cross-sectional reduction of the mechanically weakened section of the wire.

The present invention has been shown and described for delivery and detachment of an embolic coil. Other occlusive devices are contemplated and within the scope of the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A combination delivery system and embolic coil, the system comprising:
   a delivery tube having a distal end, an opposite end, a lumen define axially therethrough;
   a proximal coil junction disposed between the delivery tube and the embolic coil; the proximal coil junction having a proximal end and an opposite distal end;
   a detachable wire having a proximal end and an opposite distal end; a terminating feature being disposed on the distal end of the wire; the wire being insertable through the lumen and extending proximally beyond the proximal end of the delivery tube; and
   at least one stretch resistant member disposed within a coil lumen formed by the embolic coil; a distal end of each of the at least one stretch resistant members being secured to a distal end of the embolic coil, while each of the at least one stretch resistant members is also secured proximate the proximal end of the embolic coil;
   wherein the proximal coil junction comprises a two piece mating adapter including a first component secured to the distal end of the delivery tube and a second component secured to the proximal end of the embolic coil; the two-piece mating adapter having a first channel defined longitudinally therethrough for receiving therein the terminating feature of the wire and a second channel defined traverse to and intersecting with the first channel; the system further comprises a coil connecting member receivable in the second channel and threadable through the terminating feature of the wire.

2. A method for using a combination delivery system and embolic coil, wherein the combination delivery system and embolic coil includes: a delivery tube having a distal end, an opposite proximal end, a lumen defined axially therethrough; a proximal coil junction disposed between the delivery tube and the embolic coil; the proximal coil junction having a proximal end and an opposite distal end; a detachable wire having a proximal end and an opposite distal end; a terminating feature being disposed on the distal end of the wire; the wire being insertable through the lumen and extending proximally beyond the proximal end of the delivery tube; and at least one stretch resistant member disposed within a coil lumen formed by the embolic coil; a distal end of each of the at least one stretch resistant members being secured to a distal end of the embolic coil, while each of the at least one stretch resistant members is also secured proximate the proximal end of the embolic coil; wherein the distal end of the delivery tube is retained by the wire physically against without being attached in any way to the proximal junction; wherein the proximal coil junction comprises a two piece mating adapter including a first component secured to the distal end of the delivery tube and a second component secured to the proximal end of the embolic coil; the two-piece mating adapter having a first channel defined longitudinally therethrough for receiving therein the terminating feature of the wire and a second channel defined traverse to and intersecting with the first channel; the system further comprises a coil connecting member receivable in the second channel and threadable through the terminating feature of the wire, the method comprising the steps of:

removing the coil connecting member completely from the second channel of the two piece mating adapter and the terminating feature of the wire; and pulling in a proximal direction the wire to separate the second component attached to the embolic coil from that of the first component attached to the delivery tube.

* * * * *